(12) United States Patent
Liu et al.

(10) Patent No.: US 12,427,137 B2
(45) Date of Patent: Sep. 30, 2025

(54) METHOD FOR REDUCING METHANE PRODUCTION IN ANIMAL STOMACH

(71) Applicant: CHINA AGRICULTURAL UNIVERSITY, Beijing (CN)

(72) Inventors: Guoshi Liu, Beijing (CN); Yao Fu, Beijing (CN); Songyang Yao, Beijing (CN); Xiao Ma, Beijing (CN); Haiying Yu, Beijing (CN); Yujun Yao, Beijing (CN); Dongying Lv, Beijing (CN); Shengyu Guan, Beijing (CN)

(73) Assignee: China Agricultural University, Beijing (CN)

( * ) Notice: Subject to any disclaimer, the term of this patent is extended or adjusted under 35 U.S.C. 154(b) by 120 days.

(21) Appl. No.: 18/104,459

(22) Filed: Feb. 1, 2023

(65) Prior Publication Data
US 2023/0255936 A1    Aug. 17, 2023

(30) Foreign Application Priority Data
Feb. 11, 2022    (CN) .......................... 202210128296.X

(51) Int. Cl.
| | |
|---|---|
| *A61K 31/4045* | (2006.01) |
| *A23K 20/132* | (2016.01) |
| *A23K 50/10* | (2016.01) |
| *A61K 9/00* | (2006.01) |
| *A61K 31/405* | (2006.01) |
| *A61P 1/04* | (2006.01) |

(52) U.S. Cl.
CPC ........ *A61K 31/4045* (2013.01); *A23K 20/132* (2016.05); *A23K 50/10* (2016.05); *A61K 9/0056* (2013.01); *A61K 31/405* (2013.01); *A61P 1/04* (2018.01); Y02P 60/22 (2015.11)

(58) Field of Classification Search
CPC ...... A23K 20/132; A23K 50/10; A23K 50/30; A23K 50/40; A23K 50/50; A23K 50/75; A61P 1/04; A01K 67/02; A61K 9/0056; A61K 31/405; A61K 31/4045
See application file for complete search history.

(56) References Cited

U.S. PATENT DOCUMENTS

| | | |
|---|---|---|
| 6,974,841 B1 | 12/2005 | Rapisarda |
| 2021/0323917 A1 | 10/2021 | Li et al. |

FOREIGN PATENT DOCUMENTS

| | | | |
|---|---|---|---|
| CN | 102905526 A | 1/2013 | |
| CN | 103518965 | 1/2014 | |
| CN | 103766653 | 5/2014 | |
| CN | 110463838 | 11/2019 | |
| CN | 111303211 | 6/2020 | |
| KR | 980009243 A | 4/1998 | |
| WO | 2011/119544 | 9/2011 | |
| WO | WO-2012170322 A1 * | 12/2012 | ........... A23K 20/132 |

OTHER PUBLICATIONS

Brockus, K.E., Hart, C.G., Gilfeather, C.L., Fleming, B.O. and Lemley, C.O., 2016. Dietary melatonin alters uterine artery hemodynamics in pregnant Holstein heifers. Domestic animal endocrinology, 55, pp. 1-10. (Year: 2016).*
Ouyang, J., Wang, M., Bu, D., Ma, L., Liu, F., Xue, C., Du, C., Aboragah, A. and Loor, J.J., 2021. Ruminal microbes exhibit a robust circadian rhythm and are sensitive to melatonin. Frontiers in Nutrition, 8, p. 760578. (Year: 2021).*
Yao, S., Wu, H., Ma, H., Fu, Y., Wei, W., Wang, T., Guan, S., Yang, H., Li, X., Guo, J. and Lu, Y., 2020. Effects of rumen bypass melatonin feeding (RBMF) on milk quality and mastitis of Holstein cows. PeerJ, 8, p. e9147. (Year: 2020).*
Liu, Lijuan, Siyu Zhang, Jiayang Bao, Xiaowen He, Danni Tong, Cong Chen, Qingxiang Ying, Qing Zhang, Caiqiao Zhang, and Jian Li. "Melatonin improves laying performance by enhancing intestinal amino acids transport in hens." Frontiers in endocrinology 9 (2018): 426. (Year: 2018).*
First Office Action of the priority application CN202210128296X, dated Sep. 23, 2022, 13 pages.
Notification to Grant Patent Right for Invention of the priority application CN202210128296X, 3 pages.
Cao Zhen et al., Progress on Methane Mitigation in Livestock Gastrointestinal Tract, Acta Ecologiae Animals Domastici, vol. 32, No. 4, Jul. 2011, pp. 1-8.

* cited by examiner

Primary Examiner — James H Alstrum-Acevedo
Assistant Examiner — Carolyn L. Ladd
(74) Attorney, Agent, or Firm — Nixon & Vanderhye P.C.

(57) ABSTRACT

Provided is a method for reducing methane production in animal stomachs by adding melatonin to gastric juice of the animal or feeding the animal with melatonin. In the method of the present disclosure, 10-7 mol/L to 10-3 mol/L of melatonin can reduce the methane production from the in vitro gastric fermentation fluid, and feeding melatonin of 8.0 to 35.0 mg/kg/day can reduce the methane production from the animal respiration from day 7 of feeding melatonin. The method of the present disclosure can reduce greenhouse gas emissions of animals, control environmental pollution and realize low-carbon farming.

7 Claims, 12 Drawing Sheets

Chao 1

Observed_species

PD_whole_tree shannon

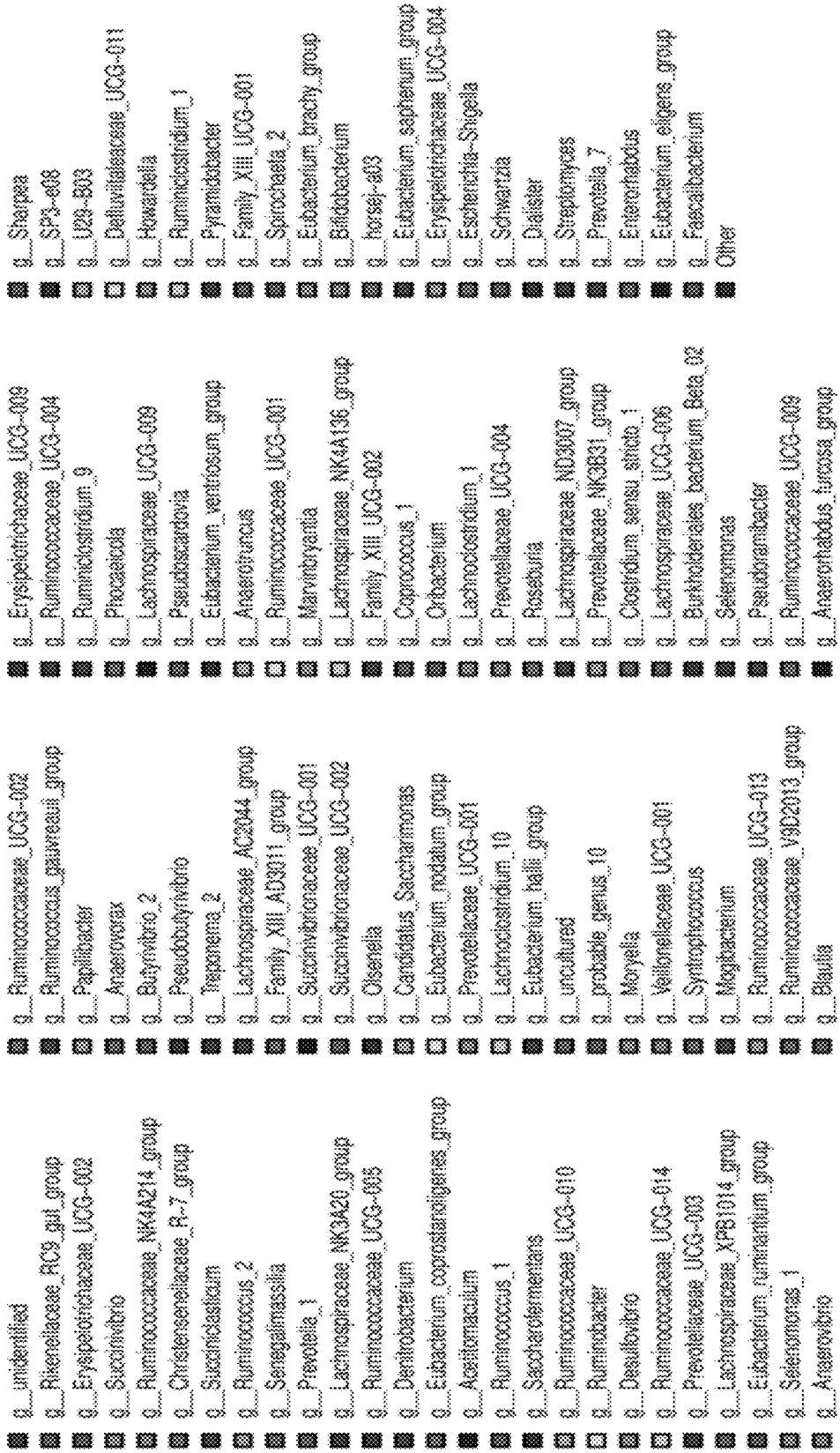

Cladogram

METHOD FOR REDUCING METHANE PRODUCTION IN ANIMAL STOMACH

CROSS-REFERENCE TO RELATED APPLICATION

The present disclosure claims priority to Chinese Application No. 202210128296X, filed on Feb. 11, 2022, which is incorporated herein by reference in its entirety.

TECHNICAL FIELD

The present disclosure relates to the field of agricultural animal husbandry technology and specifically relates to methods for reducing methane production in animal stomach by in vitro addition or in vivo feeding of melatonin.

BACKGROUND

Carbon emissions from agriculture account for 18.4% of global carbon emissions. In particular, livestock production and feces discharge account for 31.5% of agricultural carbon emissions and 5.8% of global carbon emissions. Due to rumen fermentation, ruminant animals produce more greenhouse gases than monogastric animals such as pigs and chickens. Thus, reducing methane emissions from animal stomachs is important for solving environmental problems and achieving "peak carbon dioxide emissions".

Melatonin (MT) is a neuroendocrine hormone produced by animal pineal gland. It is known that MT is involved in the regulation of biological rhythms and several physiological processes. In recent years, numerous studies have revealed that melatonin also plays an important role in regulating intestinal microorganisms, and then modulating immunity and affecting reproduction by the alteration of the morphological compositions in intestinal tracts.

The rumens of ruminant animals constitute a complex ecosystem. The rumen is similar to an anaerobic fermenter which comprises a large number of microorganisms such as bacteria, fungi, protozoa and methanogens. Such microorganisms can cooperate and degrade the fodder into $CH_4$, $CO_2$, $NH_3$ and volatile fatty acids through interactions.

Therefore, research is needed to explore a method for reducing methane production in animal stomachs so as to reduce methane emissions.

SUMMARY

In order to achieve the purpose of the present disclosure, a method for reducing methane production in animal stomachs is provided.

In the first aspect, the present disclosure provides a method for reducing methane production in a stomach of an animal, which comprises the following steps: adding melatonin, in an amount of $10^{-7}$ mol/L to $10^{-3}$ mol/L, to gastric juice of the animal; or feeding the animal with melatonin in an amount of 8.0 to 35.0 mg/kg/day.

In some embodiments, melatonin may be added to the gastric juice of the animal in an amount of $10^{-7}$ mol/L, $10^{-6}$ mol/L, $10^{-5}$ mol/L, $10^{-4}$ mol/L, or $10^{-3}$ mol/L. Preferably, melatonin may be added to the gastric juice in an amount of $10^{-5}$ mol/L to $10^{-3}$ mol/L. More preferably, melatonin may be added to the gastric juice in an amount of $10^{-3}$ mol/L.

In some embodiments, the animal may be fed with melatonin in an amount of 8.0 mg/kg/day, 8.33 mg/kg/day, 9.0 mg/kg/day, 10.0 mg/kg/day, 12.0 mg/kg/day, 12.5 mg/kg/day, 14.0 mg/kg/day, 15.0 mg/kg/day, 16.0 mg/kg/day, 16.7 mg/kg/day, 18.0 mg/kg/day, 18.75 mg/kg/day, 20.0 mg/kg/day, 25.0 mg/kg/day, 30.0 mg/kg/day, 33.3 mg/kg/day, or 35.0 mg/kg/day. Preferably, the animal may be fed with melatonin in an amount of 12.5 to 25.0 mg/kg/day. More preferably, the animal may be fed with melatonin in an amount of 15.0 to 20.0 mg/kg/day.

In some embodiments, the animal may be fed with melatonin for 7 to 21 days. Preferably, the animal may be fed with melatonin for 7 to 14 days. More preferably, the animal may be fed with melatonin for 14 days.

In some embodiments, the animal may be a monogastric or ruminant animal.

Preferably, the monogastric animal may comprise pig, chicken, duck, goose, dog, rabbit and the like.

Preferably, the ruminant animal may comprise cow, horse, sheep, camel, deer and the like. More preferably, the ruminant animal may be cow.

In some embodiments, the present disclosure provides a method for reducing methane production in a rumen of a ruminant animal, which comprises the following steps: adding melatonin, in an amount of $10^{-7}$ mol/L to $10^{-3}$ mol/L, to a rumen fluid of the ruminant animal; or feeding the ruminant animal with melatonin in an amount of 8.0 to 35.0 mg/kg/day.

In some embodiments, melatonin may be added to the rumen fluid of the ruminant animal in an amount of $10^{-7}$ mol/L, $10^{-6}$ mol/L, $10^{-5}$ mol/L, $10^{-4}$ mol/L, or $10^{-3}$ mol/L. Preferably, melatonin may be added to the rumen fluid of the ruminant animal in an amount of $10^{-5}$ mol/L to $10^{-3}$ mol/L. More preferably, melatonin may be added to the rumen fluid of the ruminant animal in an amount of $10^{-3}$ mol/L.

In some embodiments, the ruminant animal may be fed with melatonin in an amount of 8.0 mg/kg/day, 8.33 mg/kg/day, 9.0 mg/kg/day, 10.0 mg/kg/day, 12.0 mg/kg/day, 12.5 mg/kg/day, 14.0 mg/kg/day, 15.0 mg/kg/day, 16.0 mg/kg/day, 16.7 mg/kg/day, 18.0 mg/kg/day, 18.75 mg/kg/day, 20.0 mg/kg/day, 25.0 mg/kg/day, 30.0 mg/kg/day, 33.3 mg/kg/day, or 35.0 mg/kg/day. Preferably, the ruminant animal may be fed with melatonin in an amount of 12.5 to 25.0 mg/kg/day. More preferably, the ruminant animal may be fed with melatonin in an amount of 15.0 to 20.0 mg/kg/day.

In some embodiments, the ruminant animal may be fed with melatonin for 7 to 21 days. Preferably, the ruminant animal may be fed with melatonin for 7 to 14 days. More preferably, the ruminant animal may be fed with melatonin for 14 days.

In the second aspect, the present disclosure provides use of melatonin in reducing methane production in a stomach of an animal.

In some embodiments, the animal may be a monogastric or ruminant animal.

Preferably, the monogastric animal may comprise pig, chicken, duck, goose, dog, rabbit and the like.

Preferably, the ruminant animal may comprise cow, horse, sheep, camel, deer and the like. More preferably, the ruminant animal may be cow.

In some embodiments, melatonin may be added to gastric juice of the animal in an amount of $10^{-7}$ mol/L to $10^{-3}$ mol/L. In some embodiments, the animal may be fed with melatonin in an amount of 8.0 to 35.0 mg/kg/day.

In some embodiments, the animal may be fed with melatonin for 7 to 21 days. Preferably, the animal may be fed with melatonin for 7 to 14 days. More preferably, the animal may be fed with melatonin for 14 days.

In some embodiments, the present disclosure provides use of melatonin in reducing methane production in a rumen of a ruminant animal.

In some embodiments, melatonin may be added to a rumen fluid of the ruminant animal in an amount of $10^{-7}$ mol/L to $10^{-3}$ mol/L. In some embodiments, the ruminant animal may be fed with melatonin in an amount of 8.0 to 35.0 mg/kg/day.

In some embodiments, the ruminant animal may be fed with melatonin for 7 to 21 days. Preferably, the ruminant animal may be fed with melatonin for 7 to 14 days. More preferably, the ruminant animal may be fed with melatonin for 14 days.

The present disclosure has the following advantages.

(1) The present disclosure unexpectedly finds that melatonin can reduce gastric methane production in animals With extensive in vitro experiments, melatonin is found to produce methane-reducing effect by altering the contents of volatile fatty acids in the rumen fluids of ruminant animals and by reducing the abundance of most methanogenic bacteria.

(2) The present disclosure takes the ruminant animals as an example, in vitro simulates the rumen fermentation system, and adds melatonin to the fermentation system. The in vitro fermentation system is stable and has good experimental parallelism. The composition changes in the gas produced by the rumen fluids can be monitored intuitively from the in vitro fermentation system. In addition, the in vivo validation is performed by directly feeding cows with melatonin. The experimental results show that melatonin can reduce the methane production in the rumens of the ruminant animals.

(3) In the method of the present disclosure, the animals can be directly fed with melatonin. Thus, the method of the present disclosure is easy to operate, without complex fodder process. The fodder can be optionally substituted with plants which have high level of melatonin.

(4) The method of the present disclosure can use melatonin as the additive. Melatonin is natural and harmless, and has no problem such as veterinary drug residues and withdrawal period.

(5) The method of the present disclosure can reduce greenhouse gas emissions from animals, especially from ruminant animals, and control environmental pollution of cultivation plants, thereby realizing low-carbon farming.

BRIEF DESCRIPTION OF THE DRAWINGS

FIG. 5F shows the corresponding species in the species clustering analysis pattern of the microorganisms in the in vitro fermented rumen fluids.

DETAILED DESCRIPTION

Figure 1:
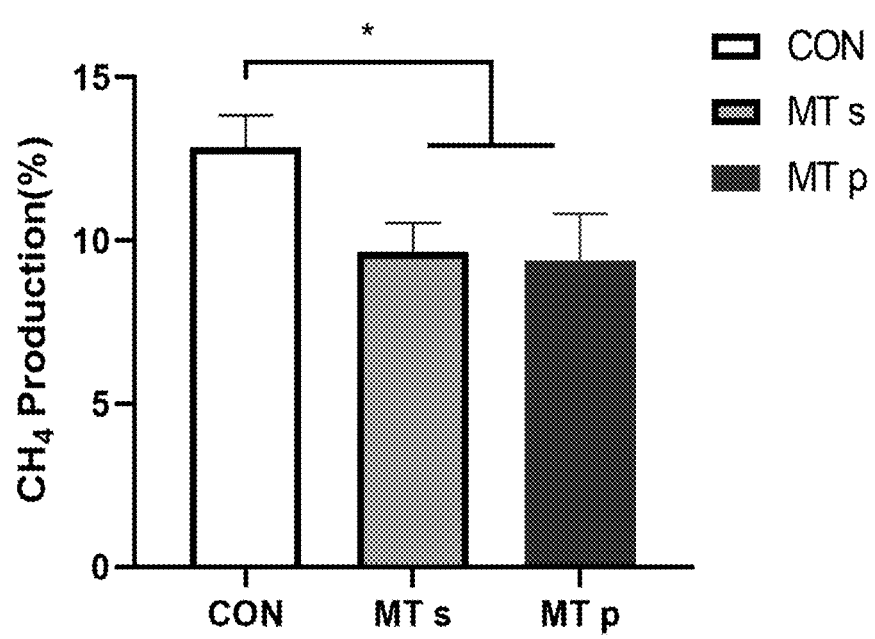
FIG. 1 shows the effects of adding melatonin in different ways on methane production.

Hereinafter, the present disclosure will be further described with reference to the following examples. These examples are merely used for illustrating the present disclosure, but not to limit the protection scope thereof.

The reagents and materials used in the following examples are commercially available products.

Example 1

1. In Vitro Fermentation of Rumen Fluids of Cows

Rumen fluids were collected from fistulated cows before morning feeding, filtered through 4 layers of gauze, and then brought back to the laboratory by placing in a thermos flask. The experiment comprised a control group (CON) and melatonin groups (MT: $10^{-3}$ mol/L, $10^{-5}$ mol/L, $10^{-7}$ mol/L). The cattle farm Total Mixed Rations (TMR) was used as the fermentation substrate, and artificial saliva was used as the matrix. Oxygen in the fermentation flasks was replaced with nitrogen. Then, the rumen fluids were incubated anaerobically at 39° C. in an incubator, which was connected to a gas bag to collect the fermentation gas. The methane content in the gas bag was detected by gas chromatography.

2. Design of Experiment

In vitro experiment: melatonin was added during the in vitro simulation of rumen fermentation.

The in vitro rumen fermentation system of 75 mL in each bottle comprises 0.5 g TMR powder, 50 mL of artificial saliva and 25 mL of filtered rumen fluid. The $10^{-3}$ mol/L, $10^{-5}$ mol/L and $10^{-7}$ mol/L melatonin groups (melatonin dissolved in a small amount of DMSO and diluted to these concentrations with saline) and a control group (only solvent, i.e., a small amount of DMSO+saline) were set up separately. For each group, the samples were collected at the fermentation times 2 h, 4 h, 8 h, 24 h and 48 h. Three replicates were set for each sample. After fermenting anaerobically at 39° C., the gas bags and fermentation liquid were collected. Gas chromatography was used to detect the methane content in the gas of the gas bags.

In vivo experiment: twenty lactating cows with similar ages and body conditions were selected and randomly divided into two groups, a control group (fed with digestible paper only) and a melatonin-fed group (fed with melatonin wrapped in digestible paper, 15 mg/kg/day). Each group had 10 cows. The cows were fed every morning after milking. The treatment lasted for 21 days. The rumen fluids were collected with rumen collection tubes before the morning feeding on days 0, 7, 14 and 21, respectively. The concentrations of melatonin in the rumen fluids were measured by liquid chromatography tandem mass spectrometry (LC-MS/MS). The breathing gas of the cows was collected by a breathing gas collection system to detect the methane content therein. Meanwhile, the information (e.g., the health condition and milk quality) of the cows was also recorded to monitor the influence of the feeding experiment on the dairy production.

3. Data Analysis

The obtained data were analyzed by one-way analysis of variance (One Way ANOVA) by means of SPSS® (Statistical Product and Service Solutions) statistical software. $p<0.05$ indicated significant difference and $p<0.01$ indicated extremely significant difference. The DunCan test was used for multiple comparisons. The results were expressed as means±SEM.

4. Experimental Results 4.1 Effects of Different Concentrations of Melatonin and Different Treatment Times on Methane Production from In Vitro Rumen Fluid Fermentation This experiment in vitro simulated the fermentation of the rumen fluids of the cows. Different concentrations of exogenous melatonin were added to the in vitro fermentation system, and the methane production was detected at different treatment time points. The results were shown in Table 1. The methane production of the rumen fermentation liquid was reduced at 4 h to 8 h of the $10^{-3}$ to $10^{-7}$ mol/L of melatonin groups. In particular, at 4 h, the methane production was reduced in all concentrations of melatonin groups by about 15% as compared with the control group. From 8 h, the $10^{-3}$ mol/L of melatonin group was more obvious in the reduction of methane production. The $10^{-3}$ mol/L of melatonin group was better in the reduction of methane production than the other melatonin groups at all time periods. This result may suggest the melatonin of the other low concentration groups was metabolized during the fermentation and its effect was gradually decreased. At 48 h, the $10^{-3}$ mol/L of melatonin group significantly reduced the methane production of the in vitro fermentation.

methane production of the in vitro rumen fluid fermentation by adding melatonin powder directly and by adding concentrated melatonin solution.

Addition form I: adding melatonin powder (MT p) directly to the fermentation system to a final concentration of $2 \times 10^{-3}$ mol/L.

Addition form II: adding concentrated melatonin solution (MT s) of $10^{-3}$ mol/L at 0 h and 24 h respectively.

After fermenting for 48 h, the methane production of these two addition forms was compared and the results were shown in FIG. 1. Both of the addition forms I and II significantly reduced the methane production of the in vitro rumen fermentation system. Further there was no significant difference between the two addition forms.

Figure 2:
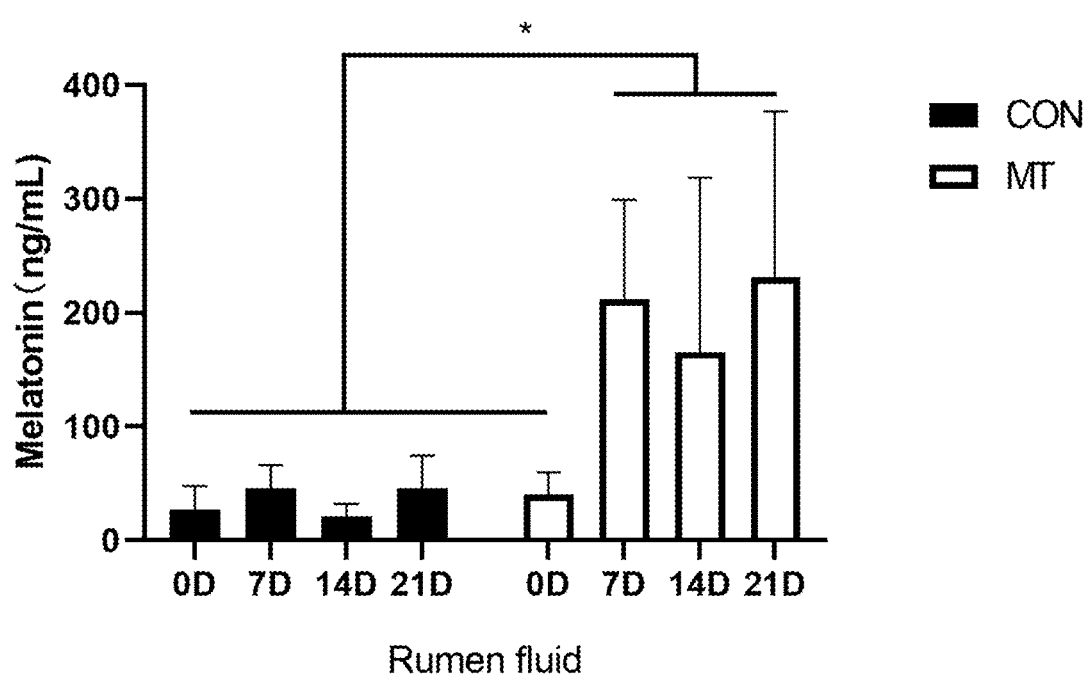
FIG. 2 shows the effects of feeding melatonin on the concentration of melatonin in the rumen fluids of cows.

4.3 Changes in Melatonin Concentrations in the Rumen Fluids of Cows which were Fed with Melatonin Twenty lactating cows with similar ages and body conditions were selected and randomly divided into two groups, a control group (CON, fed with digestible paper only) and a melatonin-fed group (MT, fed with melatonin wrapped in digestible paper). Each group had 10 cows. For the melatonin-fed group, the cows were fed, for 21 days, with melatonin powder of 15 mg/kg/day at about 15:00 every day after milking and before feeding. The rumen fluids were collected from each group at days 0, 7, 14 and 21, respectively. And the melatonin contents in the rumen fluids were determined by gas chromatography-tandem mass spectrometry. The results were shown in FIG. 2. The melatonin concentrations in the rumen fluids were significantly increased from days 7 to 21 after feeding melatonin. The results indicated that the concentrations of melatonin in rumen fluids could be increased by feeding the cows with melatonin. It in turn affected the metabolism and microorganism compositions of the rumens of the cows.

Figure 3:
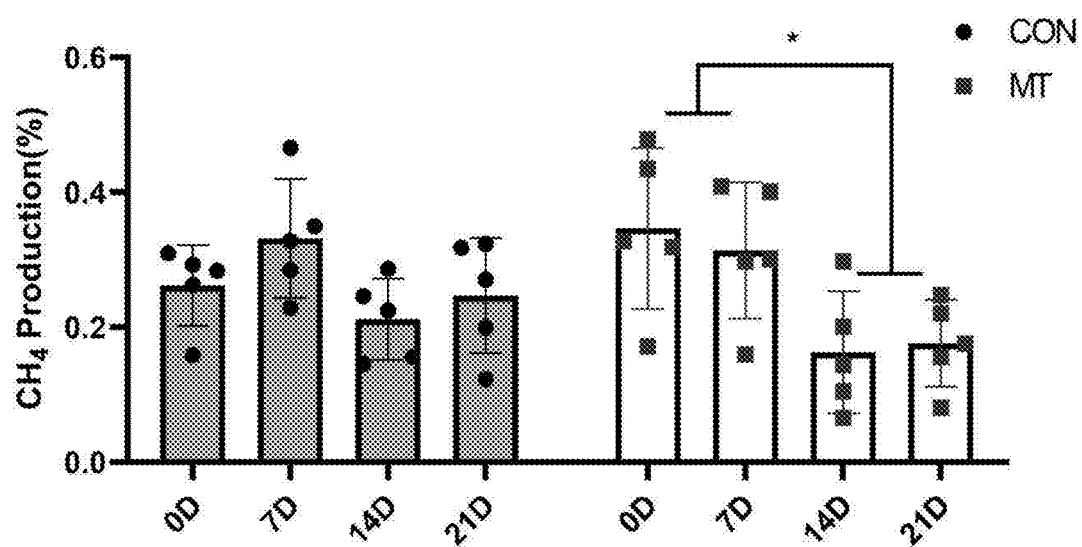
FIG. 3 shows the effects of feeding melatonin on methane production in the respiratory gases of cows.

4.4 Effect of Melatonin Feeding on the Methane Production from the Respiration of the Cows Lactating cows were fed with melatonin powder of 15 mg/kg/day for 21 days. The respiratory gases were collected from each group at days 0, 7, 14 and 21 by using a respiratory gas collection system. The methane contents in the gases were detected by gas chromatography. The results were shown in FIG. 3. The methane production from the respiration of the cows of the melatonin-fed group decreased from day 7, and decreased significantly at day 14. At day 21,

TABLE 1

Effect of melatonin on the methane production of the in vitro rumen fluid fermentation.

| fermentation time | methane content (%) | | | |
|---|---|---|---|---|
| | CON | MT $10^{-3}$ mol/L | MT $10^{-5}$ mol/L | MT $10^{-7}$ mol/L |
| 2 h | 1.06 ± 0.06 | 0.99 ± 0.05 | 1.09 ± 0.06 | 1.03 ± 0.07 |
| 4 h | 4.29 ± 0.16 | 3.42 ± 0.13 | 3.47 ± 0.07 | 3.45 ± 0.05 |
| 8 h | 5.18 ± 0.14 | 4.43 ± 0.39 | 4.47 ± 0.39 | 5.16 ± 0.14 |
| 24 h | 9.67 ± 0.25 | 9.68 ± 0.07 | 10.4 ± 0.24 | 10.6 ± 0.44 |
| 48 h | 12.56 ± 0.18$^a$ | 10.79 ± 0.53$^b$ | 12.65 ± 0.45$^a$ | 11.25 ± 0.67$^a$ |

Note:
$^{a,b}$represent significant differences, $p < 0.05$ 4.2 Effect of the Different Addition Forms of Melatonin on the Methane Production of the In Vitro Rumen Fermentation Since melatonin is metabolized in the in vitro fermentation system, and, at high concentrations, has low solubility in water, we investigated the effect of melatonin on the the methane production decreased to a similar extent as at day 14. This indicates that the methane production from the respiration of the cows can be significantly reduced by continuously feeding the cows with melatonin. In addition, this effect can be maintained for a longer period of time.

It can be known from the examples of the present disclosure that melatonin can be metabolized in the rumen fluids of the cows and high levels of melatonin can reduce methane production in the cows by altering the rumen microorganisms and metabolite contents. This result has been verified both in vivo and in vitro. Thus, the method of the present disclosure provides an operable method for reducing carbon emission during animal feeding, especially the feeding of ruminant animals.

The present disclosure is performed on the cows (normal lactating cows), and demonstrates the rumen methane production is reduced by adding melatonin to the in vitro rumen fermentation solution or directly feeding the cows with melatonin. Further, the method of the present disclosure is applicable not only to cows, but also to all methanogenic ruminant animals (including cattle, horses, sheep, camels, deer and the like) and monogastric animals (including pigs, chickens, ducks, geese, dogs, rabbits and the like).

Figure 4:
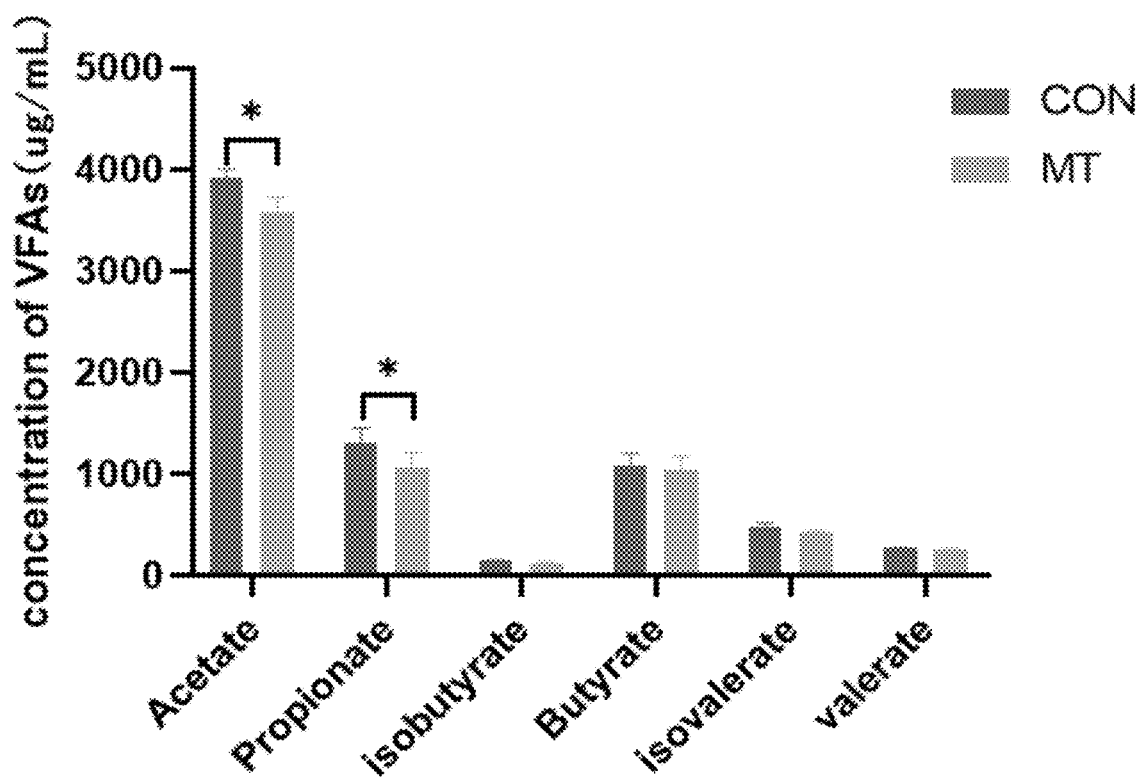
FIG. 4 shows the effects of melatonin on the volatile fatty acids in the in vitro fermented rumen fluids of cows.

Example 2. Effect of Melatonin on the Production of Volatile Fatty Acids (VFAs) from the In Vitro Rumen Fluid Fermentation Rumen microorganisms can degrade plant fibers and produce VFAs, which in turn provide energy substances to the hosts. Thus, we analyzed the production of VFAs from the in vitro fermentation system. Based on the above experiments, we determined to in vitro treat the rumen fluids with $10^{-3}$ mol/L of melatonin solution for 48 h. The levels of six VFAs (i.e., acetate (A), propionate (P), butyrate (B), isobutyrate, valerate and isovalerate), were detected in the in vitro rumen fluid fermentation solution by gas chromatography. The results were shown in FIG. 4. The levels of acetic acid and propionic acid in rumen fluids were significantly reduced after the supplementation of melatonin. In the rumens of ruminant animals, $CO_2$ and $H_2$ are mainly produced during the conversion of pyruvate into acetate and butyrate in glycolysis, and glucose can be generated from propionate. The A/P ratios of the two groups were compared, 3.00 for the control group and 3.372 for the melatonin group. The results showed that the $CH_4$ production was positively correlated with acetic acid and propionic acid, and negatively correlated with acetate/propionate (A/P). This suggests that melatonin may reduce the methane production by changing the contents of acetate and propionate.

Figure 5A:
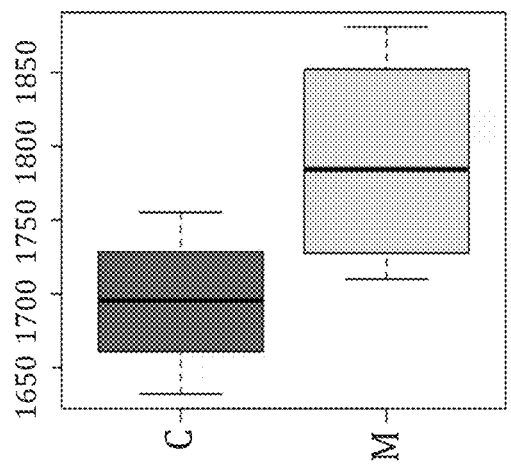
FIG. 5A shows the Chao diversity of the Alpha diversity analysis of the microorganisms in the in vitro fermented rumen fluids.
Figure 5B:
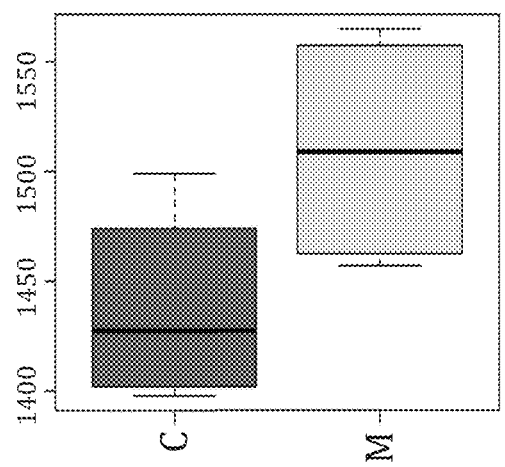
FIG. 5B shows the observed species diversity of the Alpha diversity analysis of the microorganisms in the in vitro fermented rumen fluids.
Figure 5C:
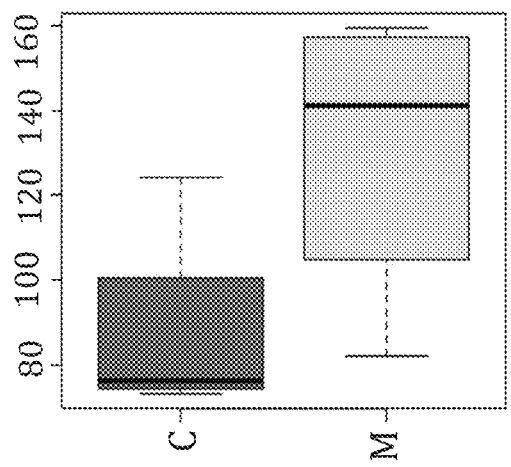
FIG. 5C shows the PD whole tree of the Alpha diversity analysis of the microorganisms in the in vitro fermented rumen fluids.
Figure 5D:
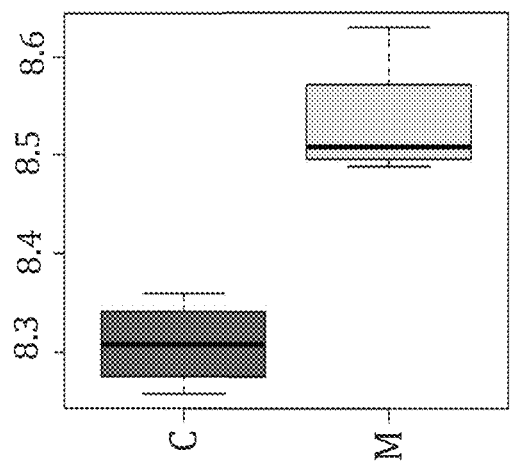
FIG. 5D shows the Shannon diversity of the Alpha diversity analysis of the microorganisms in the in vitro fermented rumen fluids.
Figure 5E:
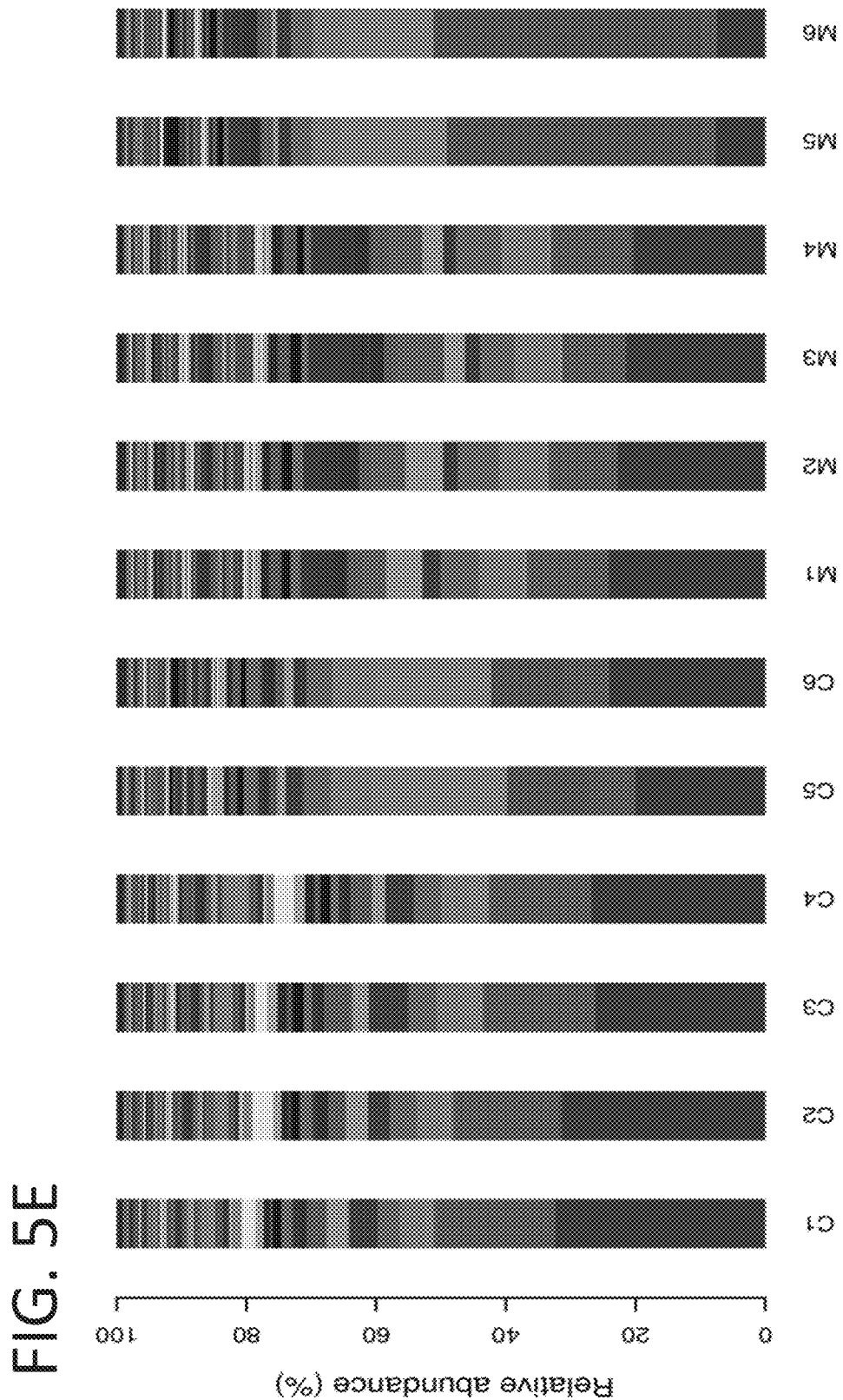
FIG. 5E shows the species clustering analysis pattern of the microorganisms in the in vitro fermented rumen fluids.

Example 3. Effect of Melatonin on the Microorganism Compositions of the In Vitro Rumen Fermentation System 1. Alpha Diversity Alpha diversity can reflect the abundance and diversity of microbial flora. As can be seen from FIGS. 5A-5D, the diversity of rumen microbial flora was increased after the addition of melatonin to the fermentation system. It indicated that melatonin did not destroy the diversity of the rumen flora. In order to clarify the species classification information of the microbial flora, the cluster analysis was performed to generate OTUs. FIGS. 5E-5F show the cluster diagram of the annotations at order level. The results show that, with melatonin treatment, the microbial flora have significant changes in the compositions, particularly in the relative abundance of the orders Clostridiales, Bacteroides, Monadales, Desulfovibrionales and the like.

2. Differential Species Analysis

Figure 6A:
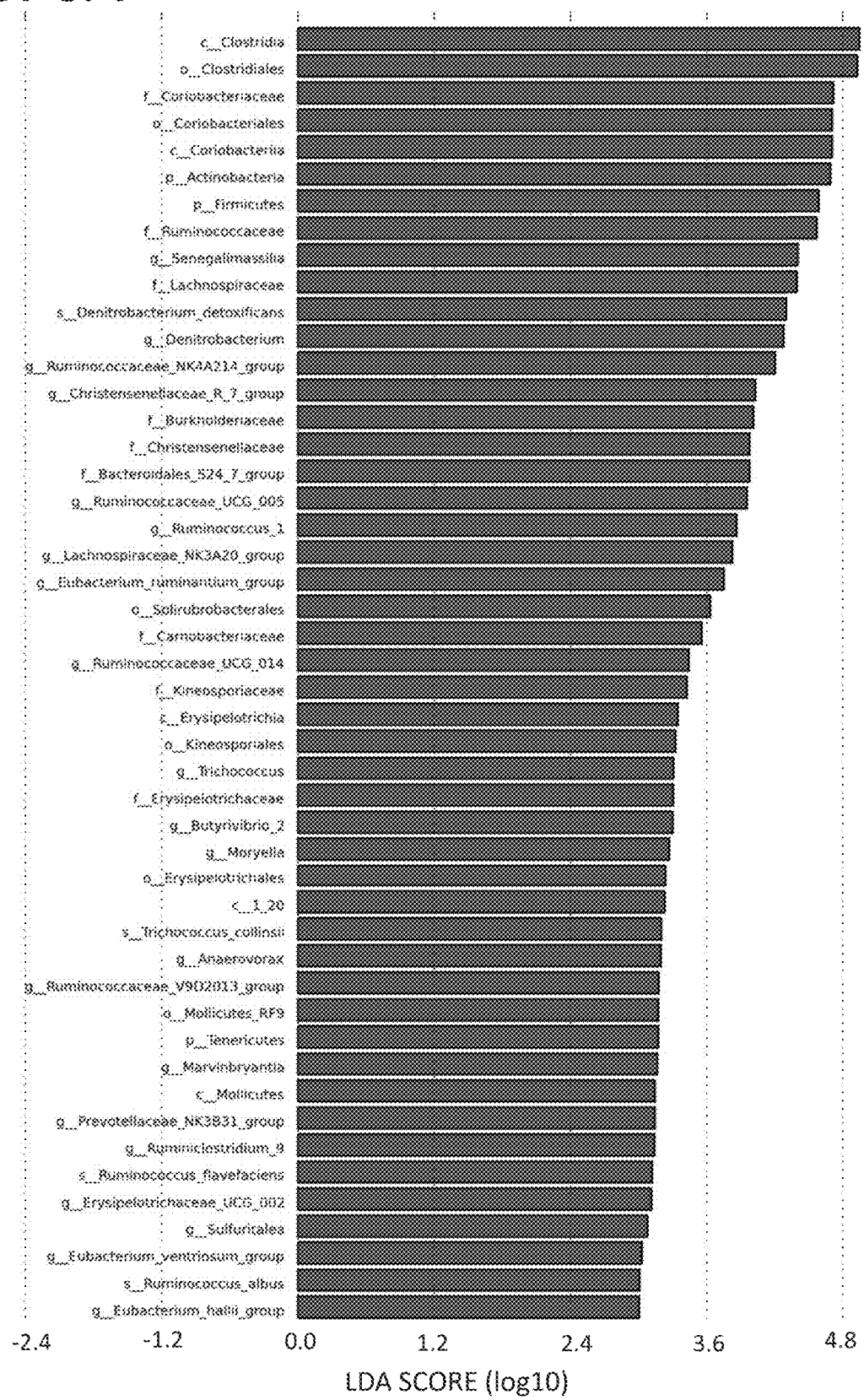
FIG. 6A shows the Beta diversity analysis of the microorganisms in the in vitro fermented rumen fluids.
Figure 6B:
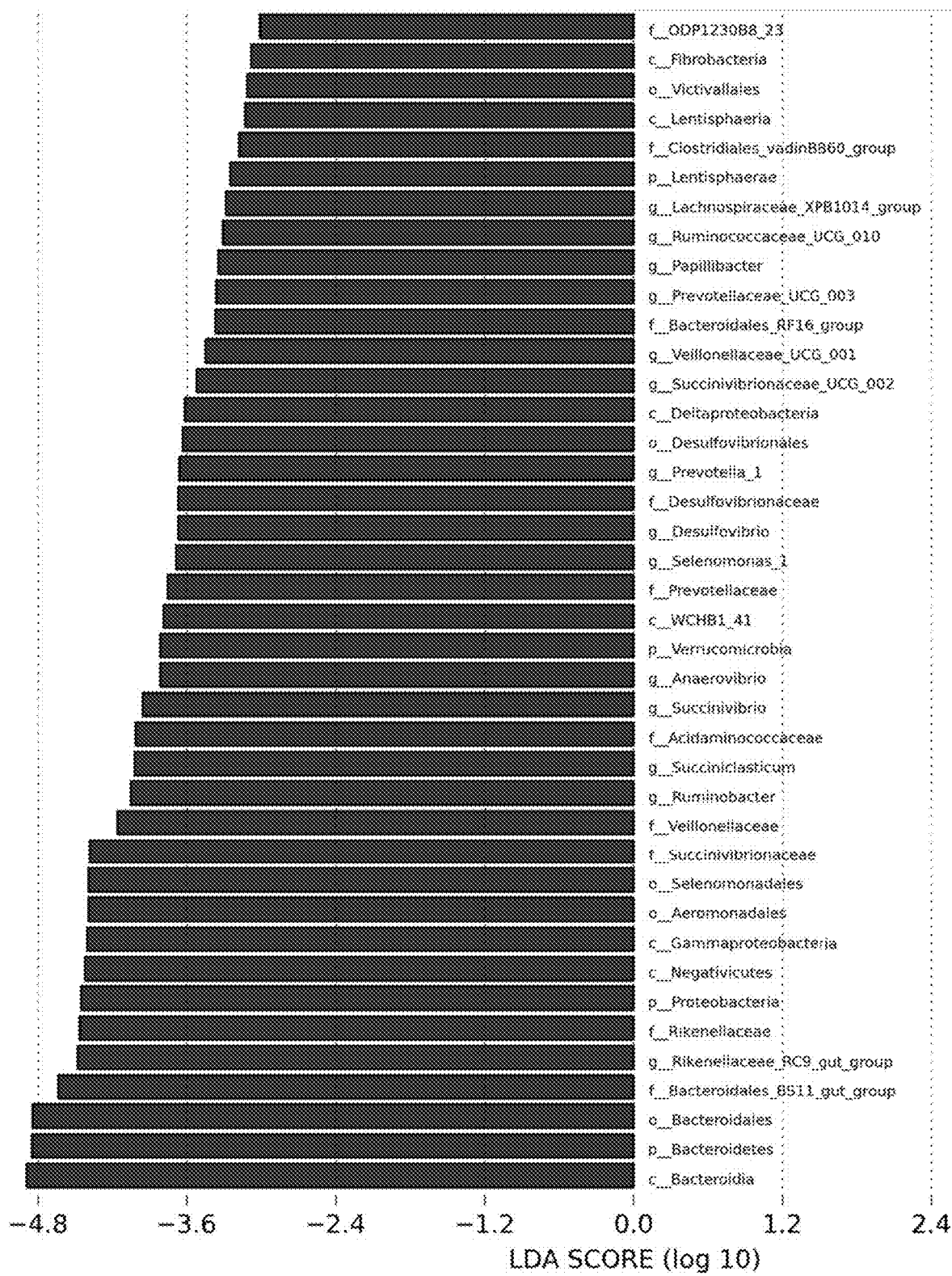
FIG. 6B shows the Beta diversity analysis of the microorganisms in the in vitro fermented rumen fluids.
Figure 6C:
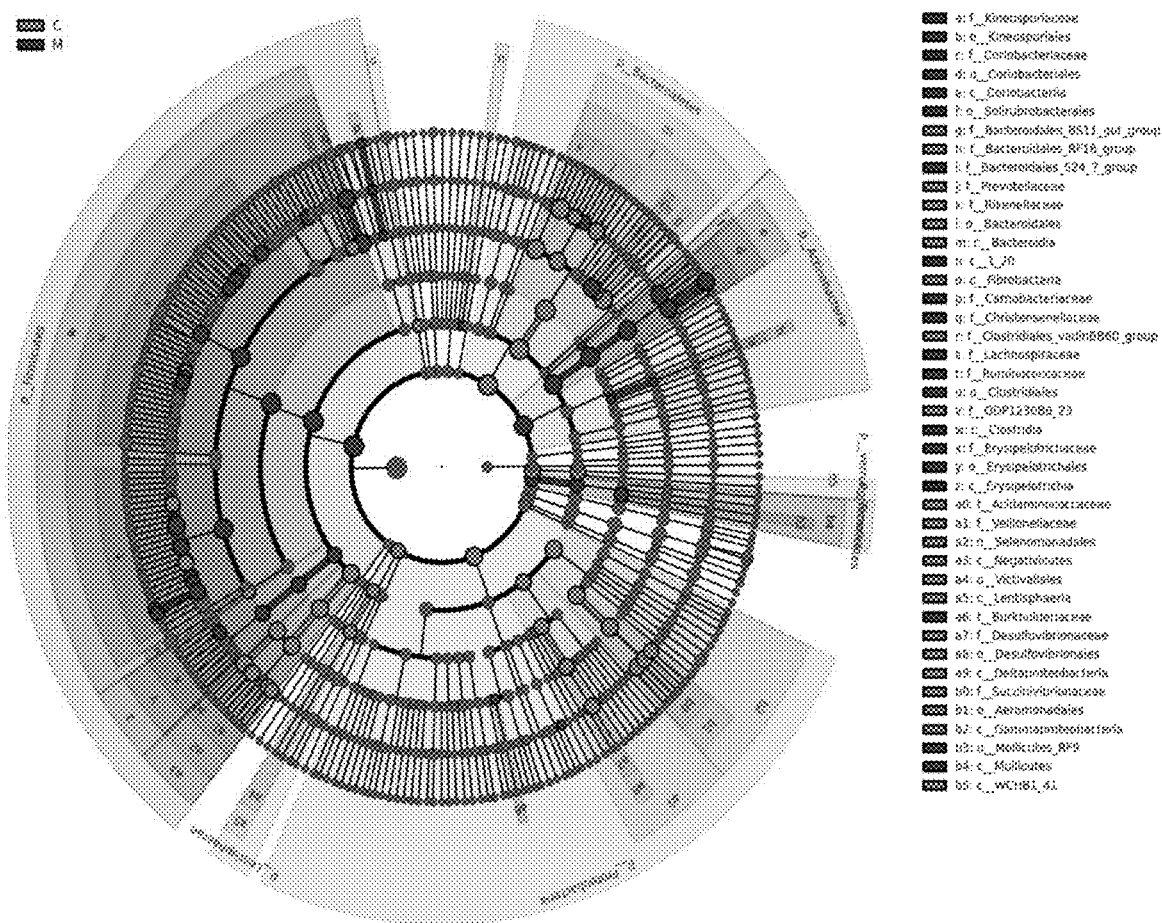
FIG. 6C shows the Cladogram of the Beta diversity analysis of the microorganisms in the in vitro fermented rumen fluids.

The analysis results were shown in FIGS. 6A-6B. There were significant differences in the relative abundance of Clostridiales, Bacteroides, Monadales, Desulfovibrionales and the like. The abundance of the microbial flora (e.g. *Prevotella* spp. and *Succiniclasticum* spp.) producing propionate and butyrate decreased, while the abundance of the microbial flora (e.g., *Bifidobacterium*) producing acetate increased. FIG. 6C shows more visually the differences among the different taxonomic groups. Each circle represents a species at the specific taxonomic level, and the size of the circle is positively correlated with the relative abundance of the species. The species with no significant differences are uniformly colored yellow, and the biomarkers for the species with differences are indicated with the color of the corresponding group.

3. Metagenome Annotations for Species

Figure 7A:
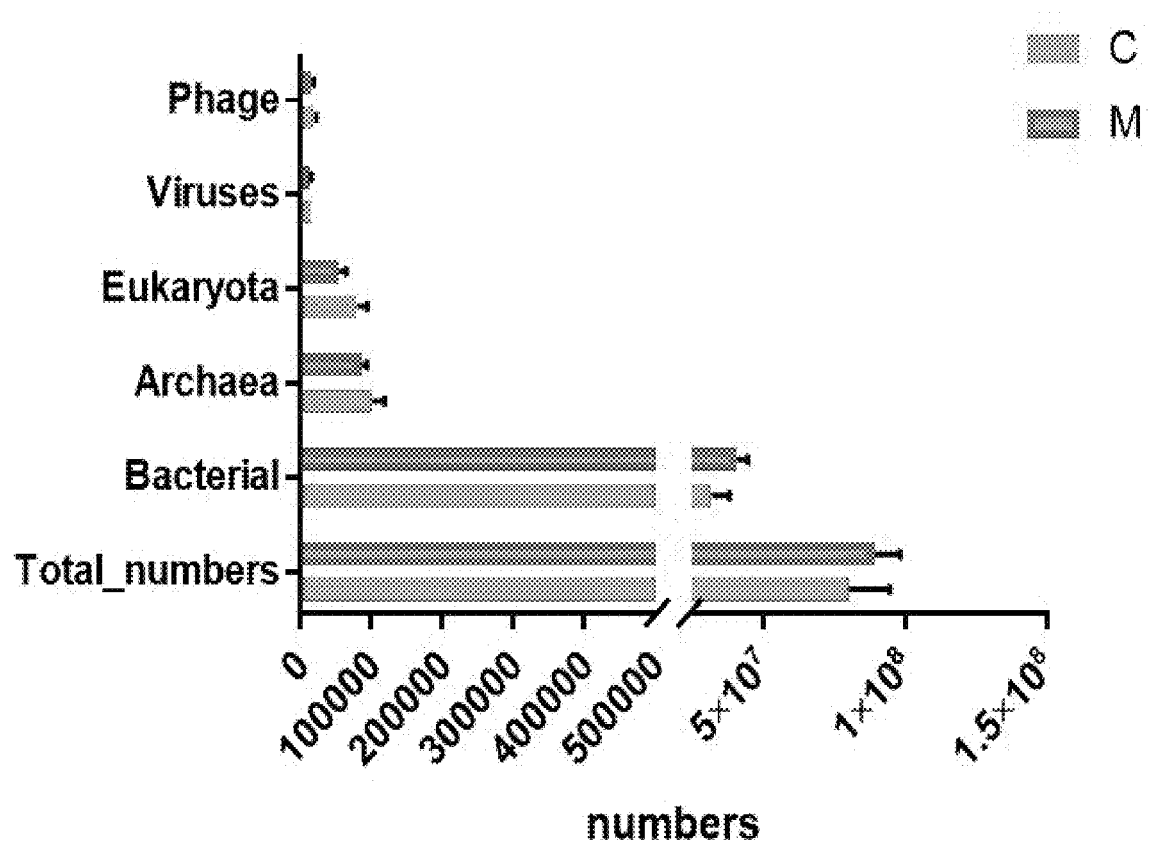
FIG. 7A shows the variation statistical diagram of archaea in the in vitro fermentation rumen fluids.
Figure 7B:
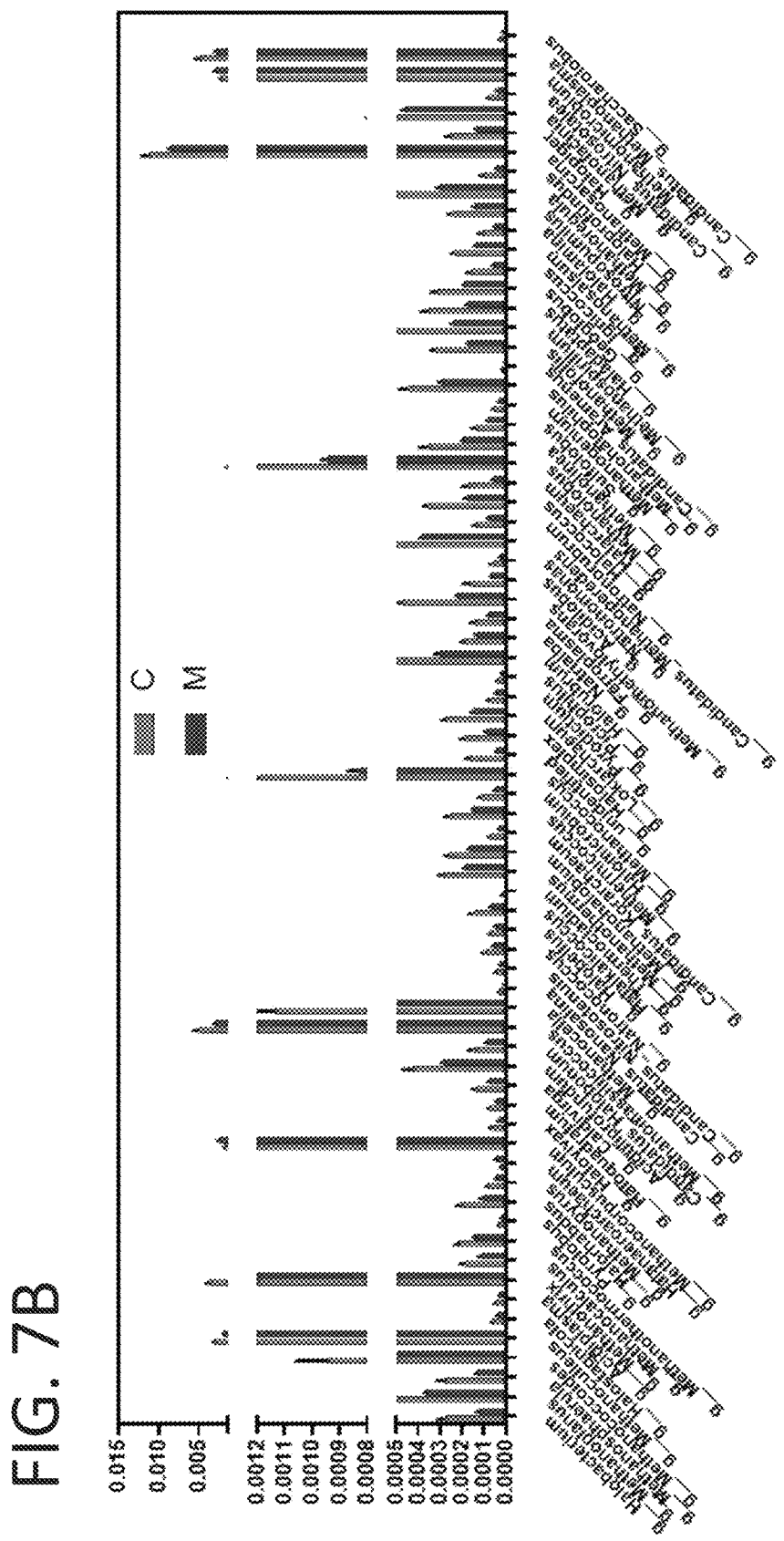
FIG. 7B shows the variation statistical diagram of archaea species in the in vitro fermentation rumen fluids.

Metagenome sequencing was performed in order to further study the changes in the rumen microbial flora. In addition to the analysis of the gene table, the metagenome sequencing can also analyze the microbial compositions of the samples. Thus, it can obtain more information on the species, including phages, viruses, fungi, archaea and the like, other than bacteria. As can be seen from FIG. 7A, the microorganisms identified by the metagenome sequencing for each group are dominated by bacteria, followed by archaea. Due to the discovery of the methane-reducing effect of melatonin, we focused on the changes of archaea. The results are shown in FIG. 7B. 72 species archaea species, which had different abundance between the control and melatonin groups, were screened. The results show that the melatonin treatment reduced the abundance of most methanogenic genera, including, for example, *Halobacterium* spp., *Methanoplanus* spp., *Methanococcoides* spp., *Methanoculleus* spp. and *Methanothrix* spp. Thus, melatonin can reduce the methane production by reducing the abundance of most methanogenic microbial flora.

The foregoing is only a general description of the present disclosure and a description of specific embodiments, and is not intended to limit the present disclosure in any other way. Any person skilled in the art may make any modification or variation to the technical solutions based on the disclosure of the present application. Without departing from the conception and spirit of the present disclosure, any modification or variation of the present disclosure falls within the scope of protection of the technical solution of the present disclosure.

What is claimed is:

1. A process for reducing methane production in a stomach of a ruminant animal, comprising the following steps:
   (1) adding melatonin in an amount of $10^{-7}$ to $10^{-3}$ mol/L to rumen fluids of the ruminant animal; or feeding the ruminant animal with melatonin in an amount of 12.0 to 35.0 mg/kg/day; and
   (2) detecting the methane content in the breathing gas of the ruminant animal by gas chromatography.

2. The process according to claim 1, wherein the melatonin is added to the rumen fluids in an amount of $10^{-5}$ to $10^{-3}$ mol/L.

3. The process according to claim 1, wherein the melatonin is added to the rumen fluids in an amount of 103 mol/L.

4. The process according to claim 1, wherein the animal is fed with melatonin in an amount of 15.0 to 25.0 mg/kg/day.

5. The process according to claim 1, wherein the ruminant animal is fed with melatonin for 7 to 21 days.

6. The process according to claim 1, wherein the ruminant animal is selected from the group consisting of cow, horse, sheep, camel and deer.

7. The process according to claim 6, wherein the ruminant animal is cow.

\* \* \* \* \*